United States Patent
Chung et al.

(10) Patent No.: US 7,897,722 B2
(45) Date of Patent: Mar. 1, 2011

(54) COMPOSITION OF BONE FORMATION WITH PHSRN-RGD CONTAINING OLIGOPEPTIDE

(75) Inventors: Chong-Pyoung Chung, Seoul (KR); Young Ku, Seoul (KR); Gene Lee, Seoul (KR); Jun-Hyeog Jang, Incheon (KR); Tae-Il Kim, Seoul (KR)

(73) Assignee: Seoul National University Industry Foundation, Seoul (KR)

(*) Notice: Subject to any disclaimer, the term of this patent is extended or adjusted under 35 U.S.C. 154(b) by 311 days.

(21) Appl. No.: 11/967,132

(22) Filed: Dec. 29, 2007

(65) Prior Publication Data

US 2009/0010988 A1    Jan. 8, 2009

(30) Foreign Application Priority Data

Jul. 4, 2007    (KR) .................. 10-2007-0066935

(51) Int. Cl.
*A61K 38/00* (2006.01)
*A61K 51/00* (2006.01)

(52) U.S. Cl. .................. 530/324; 514/1.1; 424/1.69

(58) Field of Classification Search .................. None
See application file for complete search history.

(56) References Cited

FOREIGN PATENT DOCUMENTS

| | | | |
|---|---|---|---|
| KR | 20030088257 A1 | * | 11/2003 |
| KR | 1020030088257 A1 | | 11/2003 |

OTHER PUBLICATIONS

Aota, Shin-Ichi, et al., "The short amino acid sequence pro-his-ser-arg-asn in human fibronectin enhances cell-adhesive function", "The Journal of Biological Chemistry", Oct. 7, 1994. pp. 24756-24761, vol. 269, No. 40.

Brugnami, F., et al., "Histologic evalutation of human extraction sockets treated with demineralized freeze-dried bone allograft (DFDBA) and cell occlusive membrane (Abstract Only)", "J. Periodontol.", 1996, pp. 821-825, vol. 67, No. 8, Publisher: Tufts University School of Dental Medicine.

Carrell, Nadia A. et al., "Structure of human platelet membrane glycoproteins IIb and IIIa as determined by electron microscopy", "The Journal of Biological Chemistry", Feb. 10, 1985, pp. 1743-1749, vol. 260, No. 3, Publisher: The American Society of Biological Chemists, Inc.

Globus, R. K., et al., "Fibronectin is a survival factor for differentiated osteoblasts", "Journal of Cell Science", 1998, pp. 1385-1393, vol. 111, Publisher: The Company of Biologists Limited.

Gronthos, S., et al., "Integrin-mediated interactions between human bone marrow stromal precusor cells and the extracellular matrix (Abstract Only)", "Bone", Feb. 2001, p. 174-181, vol. 28, No. 2.

Misch, C. E., et al., "Bone-grafting materials in implant dentistry (Abstract Only)", "Implant Dent.", 1993, pp. 158-167, vol. 2, No. 3.

Petrovic, Ljubinko, et al., "Different substitute biomaterials as potential scaffolds in tissue engineering (Abstract Only)", "International Journal of Oral and Maxillofacial Implants", Mar./Apr. 2006, pp. 225-231, vol. 21, No. 2.

Pierschbacher, Michael D., et al., "Cell attachment activity of fibronectin can be duplicated by small synthetic fragments of the molecule (Abstract Only)", "Nature", May 3, 1984, pp. 30-33, vol. 309.

Benoit, D. et al., "The effect on osteoblast function of colocalized RGD and PHSRN epitopes on PEG surfaces.", "Biomaterials (Abstract Only Available)", Sep. 2005, pp. 5209-5220, vol. 26, No. 25.

* cited by examiner

*Primary Examiner* — Maury Audet
(74) *Attorney, Agent, or Firm* — Steven J. Hultquist; Kelly K. Reynolds; Intellectual Property, Technology Law

(57) ABSTRACT

A PHSRN-RGD-containing oligopeptide and a composition for promoting bone formation, which contains such oligopeptide as an effective ingredient. The oligopeptide promotes osteoblastic cell adhesion and differentiation and enhances bone regenerative ability, so that the inventive oligopeptide can be effectively used in regenerative treatment of bone tissue and periodontal tissue.

6 Claims, 3 Drawing Sheets

COMPOSITION OF BONE FORMATION WITH PHSRN-RGD CONTAINING OLIGOPEPTIDE

CROSS-REFERENCE TO RELATED APPLICATION

This application claims priority under 35 USC 119 of Korean Patent Application No. 10-2007-0066935 filed Jul. 4, 2007. The disclosure of said Korean Patent Application is hereby incorporated herein by reference in its entirety, for all purposes.

BACKGROUND OF THE INVENTION

1. Field of the Invention

The present invention relates to a PHSRN-RGD containing oligopeptide and a composition for promoting bone formation, which comprises the same as an effective ingredient, and, more particulary, an oligopeptide, in which a linker peptide is inserted between PHSRN and RGD, and a composition for promoting bone formation, which contains the same as an effective ingredient.

2. Background of the Related Art

Bone defects due to pathological resorption can be restored using several types of bone graft materials. Autogenous bone graft has been referred to as the gold standard (Misch, C. E., *Implant. Dent.*, 2:158-167, 1993). However, because of its limited availability, osteoinductive materials have been developed as alternative candidates for osteoblast attraction and proliferation, but they still have provoked possible antigenicity and fostered poor bone formation (Brugnami et al., *J. Periodontol.*, 67:821-825, 1996). These limitations have led to the development of many types of osteoconductive bone replacement materials having only a scaffold function (Petrovic et al., *Int. J. Oral. Maxillofac. Implants*, 21:225-231, 2006). In this context, reliable bone regeneration requires the additional application of suitable bioactive substances to the surface of the grafted material in order to enhance osteoblast differentiation and proliferation.

It is well known that fibronectin (FN), which is present in the extracellular matrix of bone, promotes osteoblastic cell proliferation and differentiation (Globus et al., *J. Cell Sci.*, 111:1385-1393, 1998). Owing to adverse reactions such as immunogenicity and instability on enzymatic degradation, however, whole FN protein usage for osteoblast promotion is inadvisable. FN exerts various cellular functions through integrin binding, which is mediated by the consensus site including the RGD sequence located in the tenth type III domain and the PHSRN motif residing in the ninth type III module as a synergistic site (Aota S., Nomizu M. and Yamada K. M., *J Biol Chem*, 269:2456-2461,1994). Recently, it has been reported that recombinant FN supported osteoblast adhesion at levels comparable with plasma FN (Cutler and Garcia 2003).

SUMMARY OF THE INVENTION

It is an object of the present invention to provide a PHSRN-RGD containing oligopeptide and a composition for promoting bone formation, which contains the same.

To accomplish the above object, the present invention provides an oligopeptide consisting of PHSRN-L-RGD (wherein, L is a linker peptide consisting of 15~25 amino acids) and a composition for promoting bone formation, which contains the same as an effective ingredient.

The present invention also provides a bone graft material and a tissue engineering scaffold, which have an oligopeptide for promoting bone formation coated on its surface.

Another features and embodiments of the present invention will be more clarified from the following detailed description and the appended claims.

DETAILED DESCRIPTION OF THE INVENTION, AND PREFERRED EMBODIMENT

Figure 1:
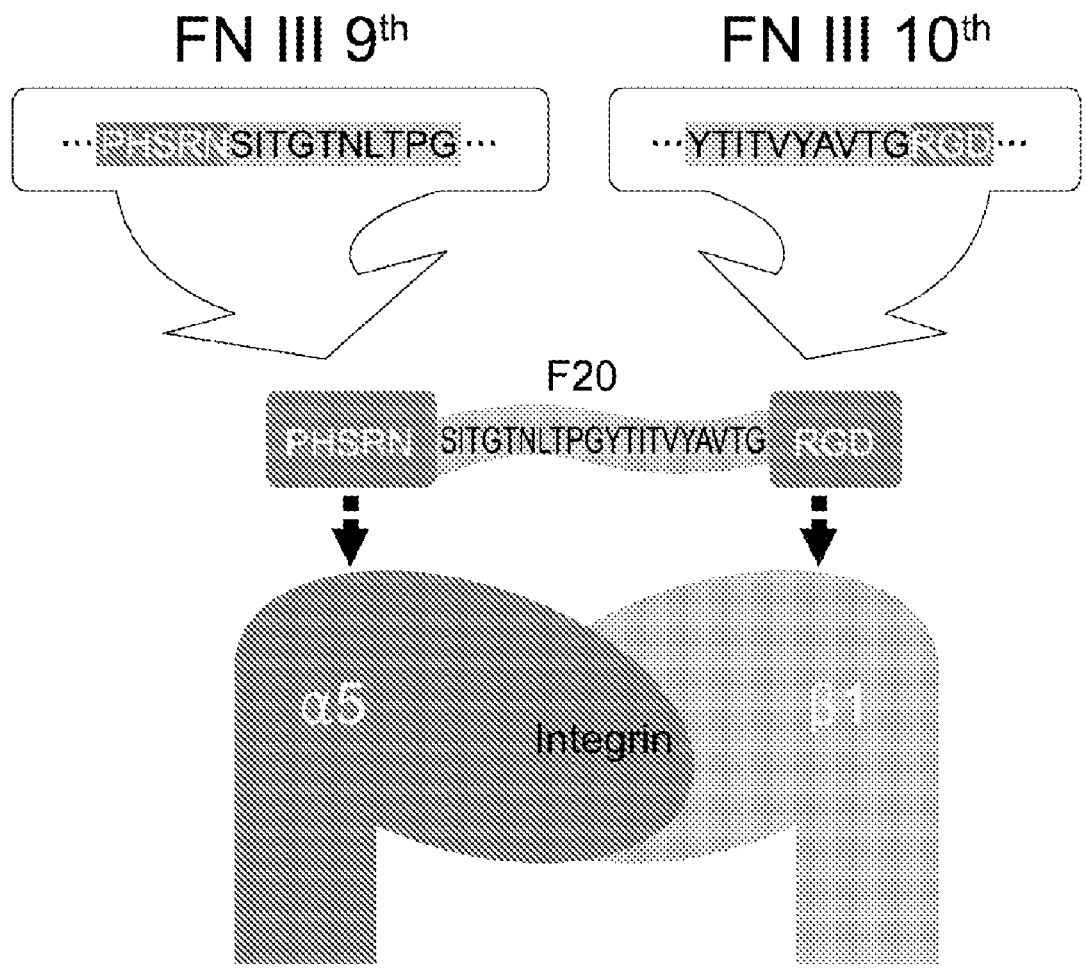
FIG. 1 is a schematic diagram of a recombinant oligopeptide (F20) binding to integrin (FN: Fibronectin).

Cell interaction with extracellular matrix protein is paramount in osteoblast functioning, which is mediated by integrins, that is, $\alpha_1\beta_1, \alpha_2\alpha_1, \alpha_3\beta_1, \alpha_4\beta_1, \alpha_5\beta_1, \alpha_6\beta_1, \alpha_8\beta_1$, and $\alpha_v\beta_3$ (Gronthos, et al., *Bone*, 28:174-181, 2001). Particularly, FN is essential for osteoblast survival and mineralization (Globus et al., *J Cell Sci.*, 111:1385-1393, 1998).

Fibronectin, which is one of the main components of the extracellular matrix in the body, is a dimer consisting of polypeptides each with a molecular weight of 220,000~240, 000 Da linked by disulfide bonds, and is involved in important biological functions such as cell adhesion, transfer, differentiation and generation. It is known that, although it is a macromolecule, in cell adhesion mediated by integrin, Arg-Gly-Asp (RGD) peptide located in the tenth domain of type III, is involved in adhesive function (Pierschbacher and Ruoslahti, *Nature*, 309:30-33, 1984), and Pro-His-Ser-Arg-Asn (PHSRN) peptide of SEQ ID NO: 1, residing in the ninth domain of type III, which includes immediate vicinity sequences, shows a synergetic effect (Aota S. et al., *J. Biol. Chem.*, 269:2456-2461, 1994). According to a model of RGD and PHSRN binding to integrin $\alpha_5\beta_1$, it is known that the width of an integrin head is 10~12 nm and the RGD and PHSRN sites are separated by 32~35 Å, a distance which one integrin molecule could span (Carrell et al., 1985, *J Biol Chem.* 260: 1743-1749).

The present inventors have prepared a recombinant oligopeptide derived from FN, in which a linker is inserted between PHSRN and RGD, and as a result confirmed that the recombinant oligopeptide increases osteoblastic cell adhesion and differentiation, and enhances bone regenerative ability, thus completing the present invention In the present invention, a peptide consisting of 20 amino acids (SITGTNLTPGYTITVYAVTG; SEQ ID NO: 2) as a linker is inserted between the fibronectin adhesive consensus site RGD and the synergistic motif PHSRN to prepare a PHSRN-L-RGD oligopeptide, thus naming it "F20 (DPHSRN-SITGTNLTPGYTITVYAVTG-RGD; SEQ ID NO: 3)". As a result of analyzing the cell adhesion capacity of the F20 in the osteoblastic cells, it was found that the cell adhesion capacity on F20-coated plates was 2-fold higher than that of the control group.

In order to examine the effect of F20 on osteoblastic cell differentiation, the ALP (alkaline phosphatase) activity of MG63 cells, which are human osteosarcoma cell line, was measured, and as a result, it was found that the ALP activity of the MG63 cells on the oligopeptide (F20)-coated plates was 2.5-fold higher than that of the control plates, suggesting that F20 promotes osteoblastic cell differentiation. Because FN binds to $a_5b_1$ integrin, the results that the composition according to the present invention promotes osteoblastic cell adhesion and differentiation, suggest that it has pertinently positioned cell-binding motifs.

Moreover, in order to confirm bone regenerative ability of the F20 in vivo, a F20-coated synthetic bone graft material was transplanted into a circular calvarial defect of a rat to measure a newly-formed bone. As a result, area of newly-formed bone in circular calvarial defect filled with the F20-coated synthetic bone graft material, was significantly larger than that in the control group, which suggests that F20 promoted bone regenerative ability.

Therefore, in one aspect, the present invention relates to an oligopeptide consisting of PHSRN-L-RGD and a composition for promoting bone formation, which contains the same as an effective ingredient.

In the present invention, the oligopeptide is preferably an oligopeptide having a linker (L) inserted between the PHSRN peptide of SEQ ID NO: 1 and RGD peptide. The L is preferably a peptide consisting of 15~25 amino acids. In the case where the number of amino acids is less than 15, the PHSRN peptide and RGD peptide are too close, and in the case where the number of amino acids is more than 25, the distance between the peptides is too far. In addition, it is more preferable that the L consists of 16~24, 17~23, and 19~22 amino acids, and most preferable that it consists of 20 amino acids of SEQ ID NO: 2. However, since the linker connects PHSRN and RGD to show cell adhesion and differentiation promoting function, any peptide can be used without limitation as long as it connects PHSRN and RGD to show cell adhesion function.

The recombinant oligopeptide (F20) according to the present invention, based on FN molecule, promotes osteoblastic cell adhesion and differentiation to enhance bone formation as described above, so that it can be effectively used as bioactive bone substitute materials. Moreover, when the desired concentration of oligopeptide is administered into the site where bone formation is needed, it is activated to promote treatment effects, so that the composition according to the present invention can be effectively used in regenerative treatment of bone tissue, periodontal tissue, and the like.

The composition according to the present invention can be prepared by additionally adding at least one pharmaceutically acceptable carrier in addition to F20, for administration. As the pharmaceutically acceptable carrier, saline solution, sterilized water, linger's solution, buffer saline, dextrose solution, maltodextrin solution, glycerol, ethanol, and at least one combination thereof, may be used, and if necessary, other general additives such as antioxidants, buffer solution, bacteriostatic agents, etc., may be added. Moreover, it can be formulated in the form of an injectable formulation such as aqueous solution, suspension, emulsion, etc., an injection agent, a pill, a capsule, a granule, a powder or a tablet by additionally adding diluent, dispersing agent, surfactant, binder and lubricant. Furthermore, it is possible to preferably formulize according to each disease or ingredients using a method, which is taught in Remington's Pharmaceutical Science or Mack Publishing Company, Easton Pa., as a suitable method in the art.

The inventive composition can be administered orally or parenterally (for example, intravenous or subcutaneous injection, or local administration) according to the desired purpose, and the dosage varies according to patient's weight, age, sex, condition, diet, its administration time, administration method, excretion rate, severity of disease and the like.

In other aspect, the present invention relates to a bone graft material and a tissue engineering scaffold, which have the oligopeptide for promoting bone formation coated on its surface.

As bone graft materials and polymer scaffolds that can be used in the present invention, all kinds of bone graft materials and polymer scaffolds, used in the art, can be used, and bone mineral powders derived from autologous bone, bovine bone, and porcine bone and porous blocks, synthetic hydroxyapatite powders and porous blocks, tricalcium phosphate powders and porous blocks, monocalcium phosphate powders and porous blocks, bone graft materials containing silicon dioxide(silica), bone-packing graft materials consisting of a mixture of silica and polymer, fine particles and porous scaffolds made from biocompatible polymers such as polylactic acid and chitosan, titanium, and three-dimensional porous scaffolds, etc., can be preferably used, but it is not limited thereto. Herein, the surface of bone graft materials and scaffolds is preferably modified so that bioactive peptide can be easily attached.

It is preferable that the oligopeptide is chemically coated on the surface of bone graft material and scaffold at a concentration of 0.01~1 $\mu M/cm^2$, more preferably 0.05~0.5 $\mu M/cm^2$, and most preferably 0.1 $\mu M/cm^2$, but it is not limited thereto.

In the case where the inventive oligopeptide (F20) is fixed on the surface of a bone graft material and a scaffold, a shield membrane or an implant, to use in a surgical operation, it is activated while maintaining its desired concentration, to promote treatment effects, so that the inventive oligopeptide can be effectively used in regenerative treatment of bone tissue and periodontal tissue.

EXAMPLES

The present invention will hereinafter be described in further detail by embodiments. However, it is to be understood that these embodiments can be modified into other various forms, and the scope of the present invention is not intended to be limited to such embodiments. Such embodiments are given to more fully describe the present invention for a person skilled in the art.

Particularly, in the following examples, a peptide consisting of specific sequence of 20 amino acids, as a linker peptide, was used, but the linker peptide serves to promote cell adhesion and differentiation only by connecting PHSRN and RGD, so that it is obvious to a skilled person in the art that the same result or similar result will be induced, although a peptide having different numbers of amino acids and different sequences, is used.

Example 1

Preparation of PHSRN-RGD Containing Oligopeptide

In order to prepare a PHSRN-RGD-containing oligopeptide, fibronectin cDNAs were first amplified using a human cDNA library as a template. PCR primers were designed to recognize the RGD region as well as the PHSRN region to synthesize a sense primer (20-BF, 5'-TTCATATGATC-CCCACTCTT-3'; SEQ ID NO: 4) and an antisense primer (20-KR, 5'-TTGGATCCTTAGTCTCCACG-3'; SEQ ID NO: 5). PCR was performed in a 50 μl reaction solution containing 50 mM KCl, 10 mM Tris/HCl (pH 8.3), 1.5 mM $MgCl_2$, 100 μg/Ml gelatin, 0.2 mM dNTPs, 1.25 units of Taq polymerase (Perkin-Elmer), and 50 pmol primers. The thermocycling parameters used in the PCR were as follows: annealing, 1 min at 55° C.; extension, 2 min at 72° C.; denaturation, 1 min at 94° C. After 30 cycles, amplified cDNAs were digested by BamHI and NdeI. After digestion, the PCR product was purified with a PCR purifying kit (QIAGEN, Chatsworth, Calif.). Nucleotide sequences of the inserted portion were analyzed using an automatic sequence analyzer (dideoxy terminator cycle sequencing; Applied Biosystems), and compared with the sequences in database of Genbank using a BLAST program of NCBI (National Center for Biotechnology Information, Bethesda, Md.).

The PCR product was cloned into pET15 (Novagen) with a C-terminal 6× His tag. Recombinant $FN_{PHSRN20RGD}$ containing the poly-His tag were expressed and purified using a $Ni^{2+}$ affinity column under denaturing conditions according to the manufacturer's protocol (Invitrogen, Carlsbad, Calif.). Cell lysates and the purified fusion protein were separated by SDS-PAGE (sodium dodecyl sulfate-polyacryamide gel electrophoresis), and stained with Coomassie Blue to observe.

Finally, a recombinant oligopeptide of SEQ ID NO: 3 (DPHSRN-SITGTNLTPGYTITVYAVTG-RGD) having the cell adhesion recognition motif RGD linked to the synergistic motif PHSRN by a peptide linker of SEQ ID NO: 2 (SITGT-NLTPGYTITVYAVTG), was obtained and named "F20" (FIG. 1).

Example 2

Cell Culture

MG63 cells (Korean Cell Line Bank, KCLB), used in the present invention, which is a human osteosarcoma cell line, were cultured in Dulbecco's modified Eagle's medium (DMEM) containing 10% (v/v) fetal bovine serum and 0.1% (w/v) gentamycin at 37° C., in a humidified 5% $CO_2$ incubator.

Example 3

Cell Adhesion Assay 24-well plates were coated with 0.1 μM recombinant oligopeptide or poly-L-lysine at a predetermined concentration overnight at 4° C. and blocked with PBS containing 1% (w/v) BSA for 30 min, then rinsed with PBS.

The MG63 cells were serum-starved for 24 hours, harvested in 0.02% (w/v) trypsin, 1 mM EDTA, and resuspended in DMEM. After being washed 3 times with DMEM containing 100 μg/Ml soybean trypsin inhibitor and 1% (w/v) BSA, $5×10^4$ MG63 cells in DMEM were plated in each well to culture at 37° C. for 30 min or 1 hour. Suspensions of control cells were maintained in BSA-coated plates at a given time. After 30 min, adherent cells were washed twice with PBS, fixed with 3% (w/v) paraformaldehyde, and stained with 0.25% (w/v) Crystal Violet (Sigma, USA) in 2% (v/v) ethanol/water. After washing with distilled water, the plates were allowed to dry. The absorbancy was measured at 570 nm to represent the mean±SD (standard deviation). Non-specific adhesion was determined using 1% BSA as a negative control group. Statistical analysis was carried out in triplicate and repeated 4 times independently using a Student' t-test (with 95% confidence interval), and the following statistical analysis was performed as described above.

Figure 2:
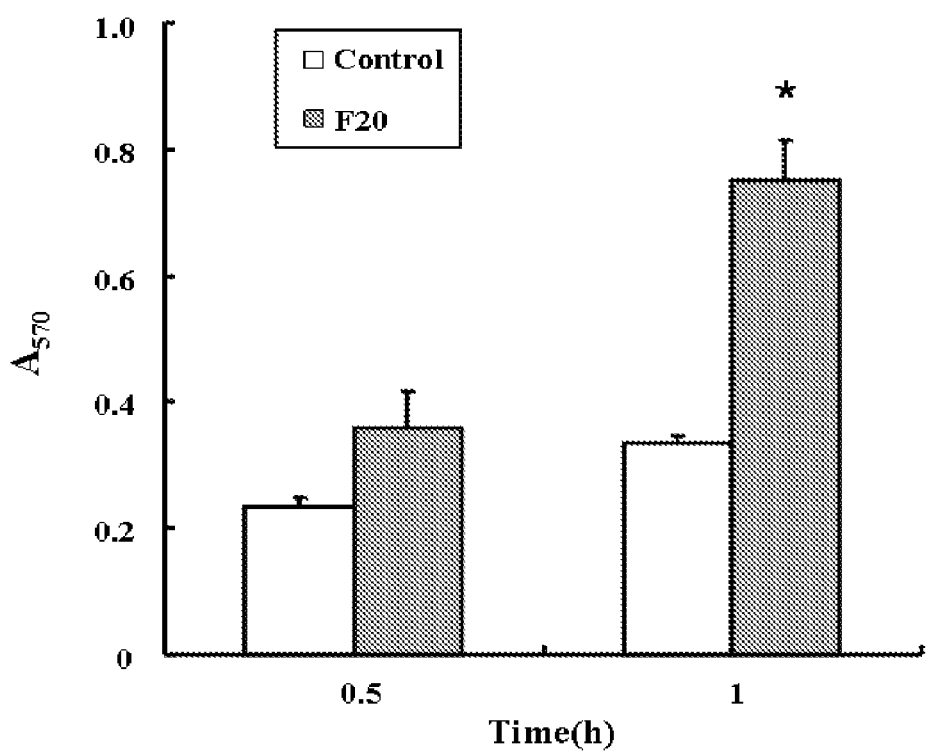
FIG. 2 is a graph quantitatively showing cell adhesion of MG63, a human osteosarcoma cell line on recombinant oligopeptide (F20)-coated culture plates (*: P<0.05; F20: recombinant oligopeptide (F20)-coated plate; and control group: poly-L-lysine-coated plate).

As a result, the oligopeptide-coated culture plates showed a 2-fold higher absorbance compared with the control plates (*: $P<0.05$, FIG. 2).

Example 4

ALP (Alkaline Phosphatase) Assay

In order to determine osteoblastic cell differentiation, ALP (Alkaline phosphatase) activity that implies in vitro bone formation activity, was measured. $5×10^4$ MG63 cells were cultured in 0.1 μM recombinant oligopeptide-coated or poly-L-lysine-coated six-well plates for 7 days. Then, they were washed with PBS and lysed in 1.5 M Tris/HCl (pH 10.2) containing 1 mM $ZnCl_2$, 1 mM $MgCl_2$ and 1% (w/v) Triton X-100 at 4° C. for 10 min. After clarifying the cell lysates by centrifugation, the ALP activity was assayed according to the manufacturer's protocol for the ALP assay kit (Sigma, USA).

Figure 3:
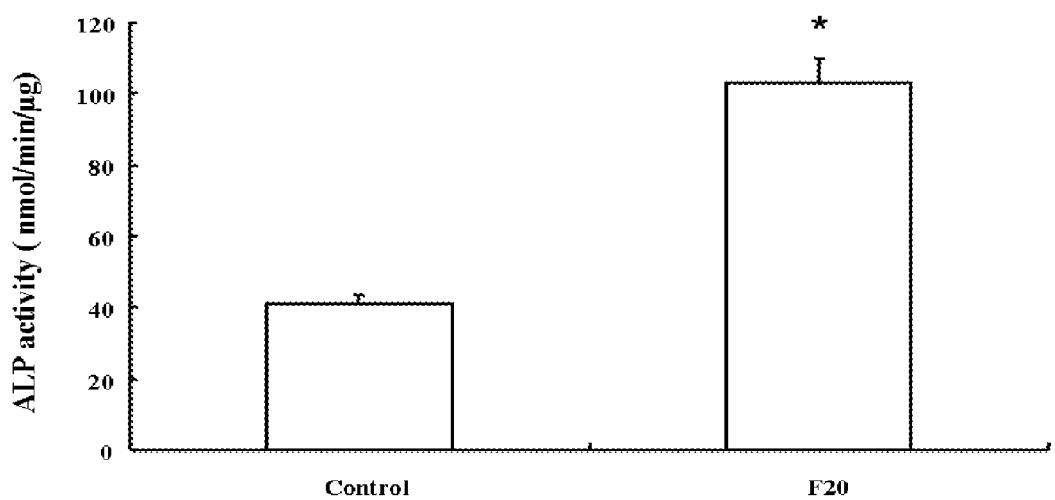
FIG. 3 is a graph showing ALP (alkaline phosphatase) activity of MG63 cells on recombinant oligopeptide (F20)-coated culture plates (*: P<0.05; F20: recombinant oligopeptide (F20)-coated plate; and control group: poly-L-lysine-coated plate).

As a result, the ALP activity of the MG63 cells on the oligopeptide (F20)-coated plates was 2.5-times higher than that of the control plates (n=3: *: $P<0.05$, FIG. 3).

Example 5

Preparation of a F20-Coated Bone Graft Material

Synthetic bone graft material particles (Bio-oss, ostehealth, USA), which were sterilized with ethylene oxide and ultraviolet ray, were added with 0.1 μM of F20 dissolved in 100 μl PBS and allowed to react for 24 hours to dry, thus prepared 0.1 μM F20-coated synthetic bone graft material.

Example 6

Bone Formation Assessment

Eight Spague-Dawley rats (Orient Bio, Korea) of 250 g were selected and received an 8 mm diameter, circular bone defect formation surgery in calvaria (Hong et al., *Biomaterials*, 27:3810-3816, 2006), and a bone graft material was transplanted into the circular bone defect to confirm bone formation.

Synthetic bone graft materials were categorized into two groups, a 0.1 μM F20-coated bone graft material group prepared in Example 5 and a non-coated control group, 50 mg of which were transplanted into the circular calvarial defect and then, periosteum and skin were separately sutured. After 3 weeks, the animals were euthanized by $CO_2$ asphyxiation. The retrieved surgical sites were fixed with a formaline solution and sectioned through the center of the circular bone defect to prepare segments with a thickness of 20 μm. The sectioned segments were Masson Trichrome stained to histometrically measure newly-formed bone using a computer-assisted image analysis system (Media cybernetics, USA).

Figure 4:
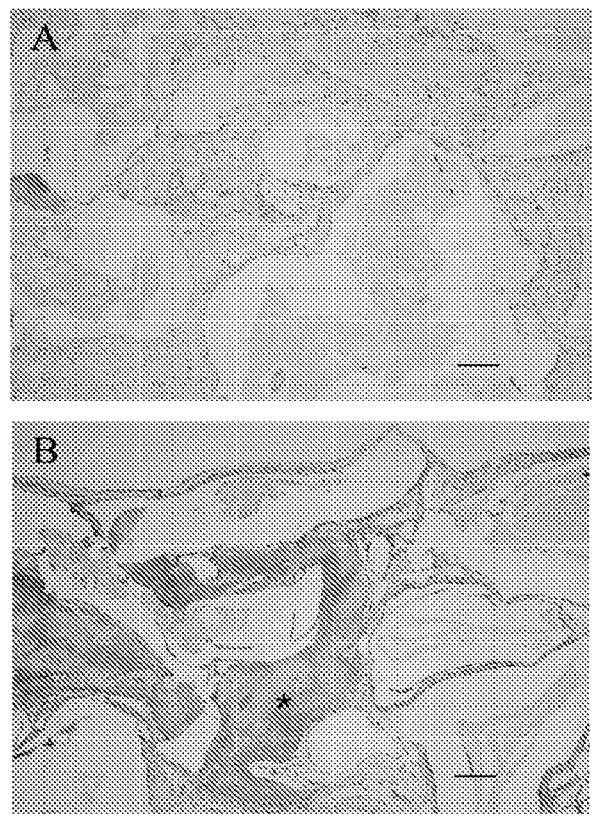
FIG. 4 shows bone regenerative ability in rat calvarial defect (A: rat calvarial bone defect model implanted with a non-coated synthetic bone graft material; B: rat calvarial bone defect model implanted with a 0.1 μm recombinant oiligopeptide (F20)-coated synthetic bone graft material; bar: 100 μm; and *: newly-formed bone)
Figure 5:
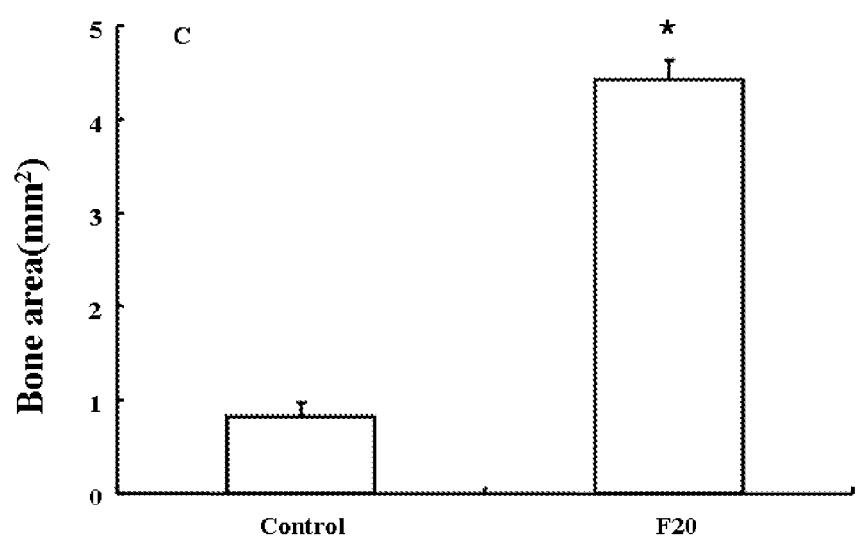
FIG. 5 is a graph quantitatively showing a newly-formed bone in rat calvarial defect implanted with a F20-coated bone graft material (*: P<0.05; control group: rat calvarial defect implanted with a non-coated bone graft material; and F20: rat calvarial defect implanted with a 0.1 μm recombinant oiligopeptide (F20)-coated synthetic bone graft material).

As a result, the area of newly-formed bone on the F20-coated synthetic bone graft material was larger than that on the non-coated control (FIG. 4, *: newly-formed bone) and, while the area of newly-formed bone in the control group was about 1 mm$^2$, that in the F20-coated synthetic bone was about 4.5 mm$^2$, thus showing that the area of newly-formed bone on the F20-coated synthetic bone showed statistically significant difference from control (FIG. 5, *: $P<0.05$; n=8).

As described above, the inventive oligopeptide promotes osteoblastic cell adhesion and differentiation and enhances bone regenerative ability, and thus it can be effectively used for promoting bone formation by fixing onto a bone graft material or tissue engineering scaffold. In addition, when a desired concentration of oligopeptide is administered into a site where bone formation is needed, it is activated to promote treatment effects, so that the inventive oligopeptide can be effectively used in regenerative treatment of bone tissue and periodontal tissue.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

What is claimed is:

1. An oligopeptide for promoting bone formation, consisting of the amino acid sequence of SEQ ID NO: 3.

2. A composition for promoting bone formation, which contains as an effective ingredient an oligopeptide consisting of the amino acid sequence of SEQ ID NO: 3.

3. A bone graft material, having the oligopeptide for promoting bone formation of claim 1 coated on its surface.

4. The bone graft material according to claim 3, wherein the bone graft material is selected from the group consisting of: organism-derived bone mineral powders and porous blocks, synthetic hydroxyapatite powders and porous blocks, tricalcium phosphate powders and porous blocks, monocalcium phosphate powders and porous blocks, bone graft materials containing silicon dioxide (silica), bone-packing graft materials consisting of a mixture of silica and polymer, fine particles and porous scaffolds containing biocompatible polymers, titanium, and three-dimensional porous scaffolds.

5. A tissue engineering scaffold, having the oligopeptide for promoting bone formation of claim 1 coated on its surface.

6. The tissue engineering scaffold of claim 5, wherein the scaffold is selected from the group consisting of: bone-packing graft materials consisting of a mixture of silica and polymer, fine particles and porous scaffolds containing biocompatible polymers, titanium, and three-dimensional porous scaffolds.

* * * * *

SEQUENCE LISTING

```
<160> NUMBER OF SEQ ID NOS: 5

<210> SEQ ID NO 1
<211> LENGTH: 5
<212> TYPE: PRT
<213> ORGANISM: Artificial
<220> FEATURE:
<223> OTHER INFORMATION: ninth domain of type III in fibronectin

<400> SEQUENCE: 1

Pro His Ser Arg Asn
1               5

<210> SEQ ID NO 2
<211> LENGTH: 20
<212> TYPE: PRT
<213> ORGANISM: Artificial
<220> FEATURE:
<223> OTHER INFORMATION: linker between RGD and PHSRN

<400> SEQUENCE: 2

Ser Ile Thr Gly Thr Asn Leu Thr Pro Gly Tyr Thr Ile Thr Val Tyr
1               5                   10                  15

Ala Val Thr Gly
            20

<210> SEQ ID NO 3
<211> LENGTH: 29
<212> TYPE: PRT
<213> ORGANISM: Artificial
<220> FEATURE:
<223> OTHER INFORMATION: recombinant oligopeptide

<400> SEQUENCE: 3

Asp Pro His Ser Arg Asn Ser Ile Thr Gly Thr Asn Leu Thr Pro Gly
1               5                   10                  15

Tyr Thr Ile Thr Val Tyr Ala Val Thr Gly Arg Gly Asp
            20                  25

<210> SEQ ID NO 4
<211> LENGTH: 20
<212> TYPE: DNA
<213> ORGANISM: Artificial
<220> FEATURE:
<223> OTHER INFORMATION: sense primer

<400> SEQUENCE: 4
ttcatatgat ccccactctt                                                 20
```

```
<210> SEQ ID NO 5
<211> LENGTH: 20
<212> TYPE: DNA
<213> ORGANISM: Artificial
<220> FEATURE:
<223> OTHER INFORMATION: antisense primer

<400> SEQUENCE: 5
ttggatcctt agtctccacg                                                    20
```